US010918906B1

(12) United States Patent
Ellsworth

(10) Patent No.: US 10,918,906 B1
(45) Date of Patent: Feb. 16, 2021

(54) MALE EXERCISE DEVICE

(71) Applicant: Evan Norman Ellsworth, Panama City Beach, FL (US)

(72) Inventor: Evan Norman Ellsworth, Panama City Beach, FL (US)

( * ) Notice: Subject to any disclaimer, the term of this patent is extended or adjusted under 35 U.S.C. 154(b) by 11 days.

(21) Appl. No.: 16/535,823

(22) Filed: Aug. 8, 2019

(51) Int. Cl.
| | |
|---|---|
| *A63B 23/00* | (2006.01) |
| *A63B 21/00* | (2006.01) |
| *A63B 21/065* | (2006.01) |
| *A63B 21/06* | (2006.01) |
| *A61F 5/00* | (2006.01) |
| *A61F 5/40* | (2006.01) |
| *A61F 5/41* | (2006.01) |
| *A63B 23/20* | (2006.01) |

(52) U.S. Cl.
CPC .......... *A63B 23/20* (2013.01); *A63B 21/0603* (2013.01); *A63B 21/065* (2013.01); *A63B 21/4039* (2015.10); *A61F 5/00* (2013.01); *A61F 5/40* (2013.01); *A61F 5/41* (2013.01)

(58) Field of Classification Search
CPC ..... A61F 5/00; A61F 5/40; A61F 5/41; A63B 21/0004; A63B 21/00058; A63B 21/00061; A63B 21/00065; A63B 21/00185; A63B 21/002; A63B 21/0023; A63B 21/0602; A63B 21/0603; A63B 21/065; A63B 21/4023; A63B 21/4025; A63B 21/4027; A63B 21/4039; A63B 21/4043; A63B 23/20; A63B 69/0057; A63B 69/0059; A63B 2225/09
See application file for complete search history.

(56) References Cited

U.S. PATENT DOCUMENTS

| | | | |
|---|---|---|---|
| 882,181 A | 3/1908 | Thomas | |
| 3,398,961 A * | 8/1968 | Higdon | A63B 69/3638 473/242 |
| 3,490,768 A * | 1/1970 | Archer | A63B 21/065 473/213 |
| 3,528,652 A * | 9/1970 | Tarbox | A63B 21/065 482/105 |
| 3,751,031 A | 8/1973 | Yamauchi | |
| 4,045,034 A * | 8/1977 | Thomas | A63B 21/0603 473/231 |
| 4,984,786 A | 1/1991 | Lemke et al. | |
| 5,547,466 A * | 8/1996 | McRoberts | A61F 5/40 2/403 |
| 5,588,940 A | 12/1996 | Price et al. | |
| 5,591,089 A * | 1/1997 | Huffines | A63B 69/3608 273/DIG. 19 |
| 6,033,374 A | 3/2000 | Miller, Jr. | |

(Continued)

*Primary Examiner* — Gary D Urbiel Goldner
(74) *Attorney, Agent, or Firm* — Peter Loffler

(57) ABSTRACT

A male exercise device uses a band made from a stretch loop material such that a section of hook material is located on the band's upper surface proximate a first end and a cooperating section of loop material is located on the band's lower surface proximate an opposing second end. A pocket depends from the band medially between the first end and the second end. Weighted pellets, such as zinc cooper pellets, are located within the pocket to provide weighting of the device. The weights can be located directly within the pocket and the pocket sealed or held within a satchel, the satchel removably disposed within the pocket.

5 Claims, 4 Drawing Sheets

(56) References Cited

U.S. PATENT DOCUMENTS

| | | | |
|---|---|---|---|
| 6,102,810 A * | 8/2000 | Boland | A63B 60/62 |
| | | | 150/160 |
| 6,419,591 B1 * | 7/2002 | Addeo | A63B 69/3638 |
| | | | 150/160 |
| 6,443,851 B1 * | 9/2002 | Liberatore | A63B 21/06 |
| | | | 150/160 |
| 6,461,249 B2 * | 10/2002 | Liberatore | A63B 69/3638 |
| | | | 473/226 |
| 6,652,387 B2 * | 11/2003 | Liberatore | A63B 21/06 |
| | | | 150/160 |
| 6,748,599 B1 * | 6/2004 | Farady | A41D 13/084 |
| | | | 2/16 |
| 7,086,998 B2 | 8/2006 | Dana, III | |
| 7,448,989 B2 | 11/2008 | Dana, III | |
| 8,162,819 B2 | 4/2012 | Adams | |
| 8,784,282 B2 | 7/2014 | Mandell | |
| 8,905,917 B2 * | 12/2014 | Tait | A61B 90/00 |
| | | | 600/38 |
| 9,173,709 B2 * | 11/2015 | Tait | A61B 90/00 |
| 9,186,545 B2 | 11/2015 | Mandell | |
| 9,504,869 B2 * | 11/2016 | Gavigan | A63B 21/0724 |
| 9,901,775 B2 * | 2/2018 | Sykes | A63B 23/025 |
| 2004/0018921 A1 | 1/2004 | Smith | |
| 2005/0252042 A1 * | 11/2005 | Harrington | A43B 5/00 |
| | | | 36/132 |
| 2009/0287041 A1 * | 11/2009 | Adams | A61F 5/41 |
| | | | 600/38 |
| 2010/0048363 A1 * | 2/2010 | Gilberti | A63B 21/065 |
| | | | 482/105 |
| 2015/0202109 A1 * | 7/2015 | Levin | A61F 5/41 |
| | | | 600/38 |
| 2017/0050072 A1 * | 2/2017 | Connelly | A63B 21/0603 |
| 2019/0201733 A1 * | 7/2019 | Marsh | A63B 21/4001 |

* cited by examiner

MALE EXERCISE DEVICE

BACKGROUND OF THE INVENTION

1. Field of the Invention

The present invention relates to a device that encircles a man's penis in order to help the man perform exercises using the device.

2. Background of the Prior Art

Dr. Arnold Kegel developed a series of exercises for women in order to help a woman deal with the physical strain of childbirth. It was later discovered that Kegel exercises performed by males helped the males achieve certain health benefits themselves. Kegel exercises for men are focused around the muscles in the prostate area of the body which are known as the pubococcygeus muscles. Exercising these muscles helps increase the length and girth of the penis, helps the person achieve firmer erections that lasted longer, helps improve overall sexual performance including heightened orgasms and longer sustained sexual performance and otherwise improves the male's overall prostate health.

There are various Kegel exercises performed by males which include squeezing and pulling of the penis as well as exercises that rely solely on the use of the pubococcygeus muscles. One aid that improves the exercises so performed is to add resistance to the penis in order to place the penis under tension which aids the muscles even when no other specific exercises are being performed.

Devices have been proposed that add resistance or tension to the penis. Such devices, which come in a wide variety of architectures and work with varying degrees of efficiency, suffer from one or more drawbacks. Many such devices are simply very complex in design and usage with several being dependent on using body parts well away from the pubic area of the user. Such complexity increases the cost of the product. Additionally, the complexity of installing the device prior to usage as well as the discomfort of being tied to other body parts, intimidates and often discourages usage of such devices. Some devices rely on cables and pulleys for their operation which cables and pulleys can be dangerous so that if an inadvertent pull on a cable or the jamming of a pulley occurs, the user can suffer significant discomfort and possibly injury. Some devices only work on either a flaccid penis or an erect penis but not both so that a user has to either remove such a device or switch between different variations of the device as the user cycles between being erect and being flaccid. Some devices, although usable in either the penis erect or penis flaccid state, nevertheless require a manual size adjustment to accommodate the current state of the penis.

What is needed is a device that provides a male penis with constant resistance in order to allow the penis to be exercised while performing Kegel type of exercises as well as when otherwise being idle with respect to the penis, which device must address the above-stated shortcomings found in the art. Specifically, such a device must of relatively simple design and construction and be confined, when installed, to the groin area of the user so as to be relatively easy and comfortable to install and use. Such a device must not rely on cables or pulleys or other similar implements that can increase the potential for discomfort and injury to the user. Such a device must be usable whether the user is erect or flaccid without the need to stop and manually adjust the device every so often.

SUMMARY OF THE INVENTION

The male exercise device of the present invention addresses the aforementioned needs in the art by providing an exercise device that helps exercise the pubococcygeus muscles of a male user in simple and straightforward fashion by providing a gravitationally assisted resistance system to the penis. The male exercise device is of relatively simple design and construction, being made using standard manufacturing techniques, so that the device is relatively inexpensive to produce so as to be economically attractive to potential consumers for this type of device. By being simple in design, the male exercise device of the present invention is easy and unintimidating to install and use without fear of hitting a cable or pulley and thereby causing injury. The male exercise device works with both a flaccid penis and an erect penis and does not need to be frequently manually adjusted between the two states or between levels of erection of the penis with the attendant change of penis girth.

The male exercise device of the present invention is comprised of a band that has a first end and a second end with a medial section disposed between the first end and the second end. The band also has an upper surface and a corresponding lower surface. The band has an outer edge extending about an outer periphery of the band. The band is formed from a stretch loop material (which may be a nylon elastomer). A section of cooperating hook material is located on the upper surface of the band proximate the first end while a section of cooperating loop material is located on the lower surface of the band proximate the second end. A pocket depends downward from the medial section of the band. A series of weight members is disposed within the pocket. The outer edge of the band is rounded. The first end of the band and the second end of the band are each rounded. The series of weight members may be metal pellets which may be zinc coated copper. The weight members are located within a satchel such that the satchel is removably received within the pocket—or the pocket may be sealed.

BRIEF DESCRIPTION OF THE DRAWINGS

Similar reference numerals refer to similar parts throughout the several views of the drawings.

DESCRIPTION OF THE PREFERRED EMBODIMENT

Figure 1:
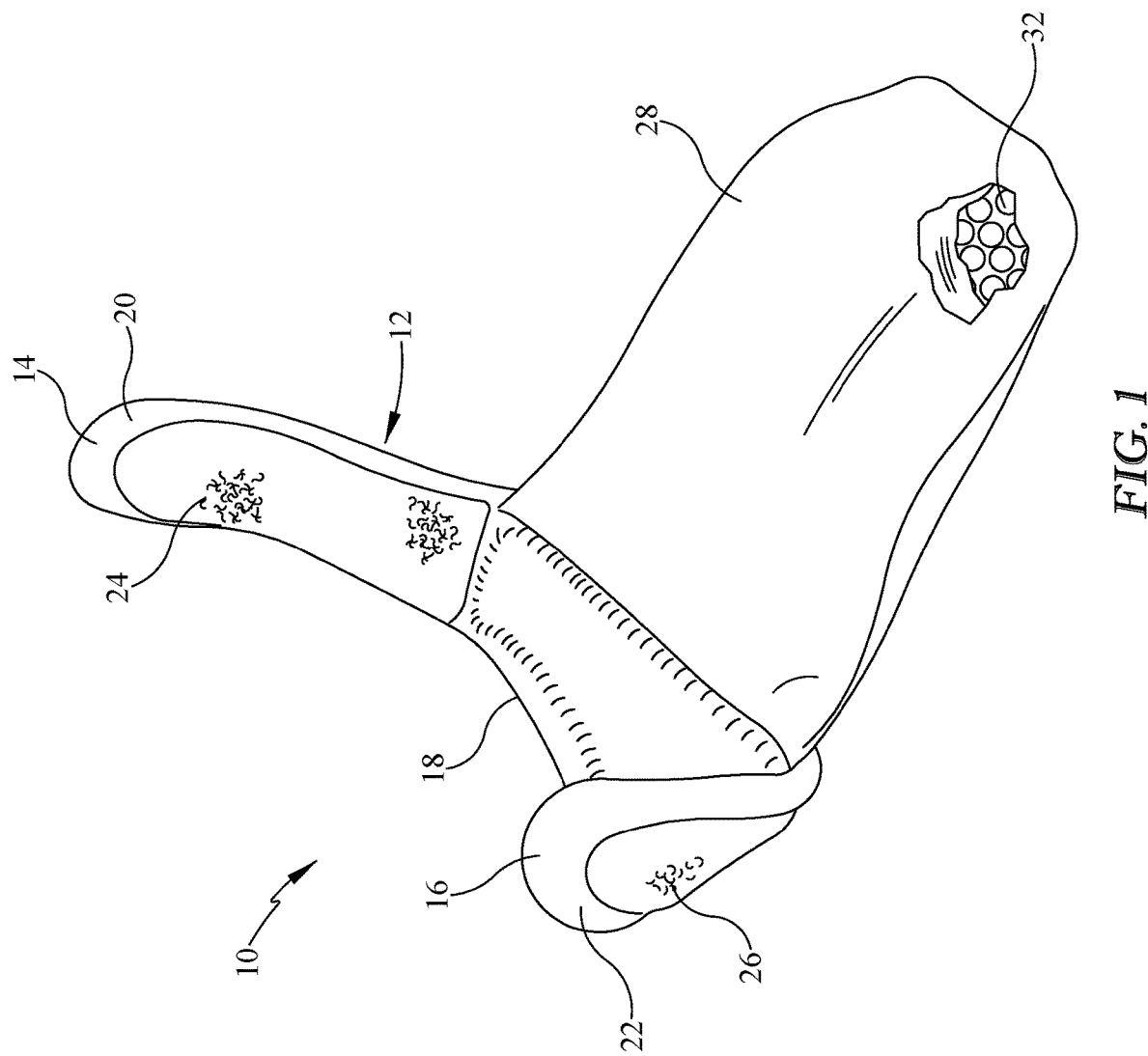
FIG. 1 is a lower perspective view, partially cutaway, of the male exercise device of the present invention.
Figure 2:
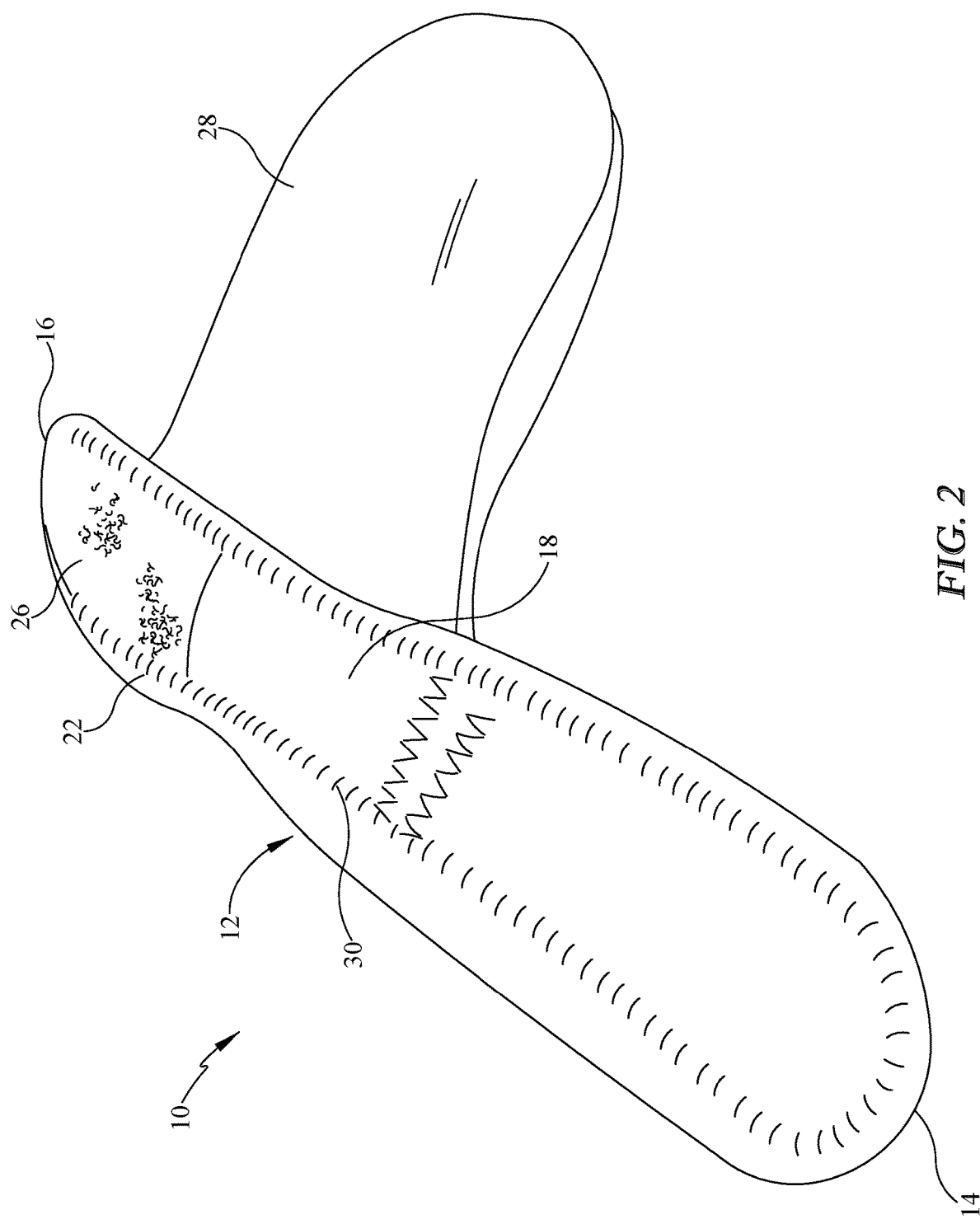
FIG. 2 is an upper perspective view of the male exercise device.
Figure 3:
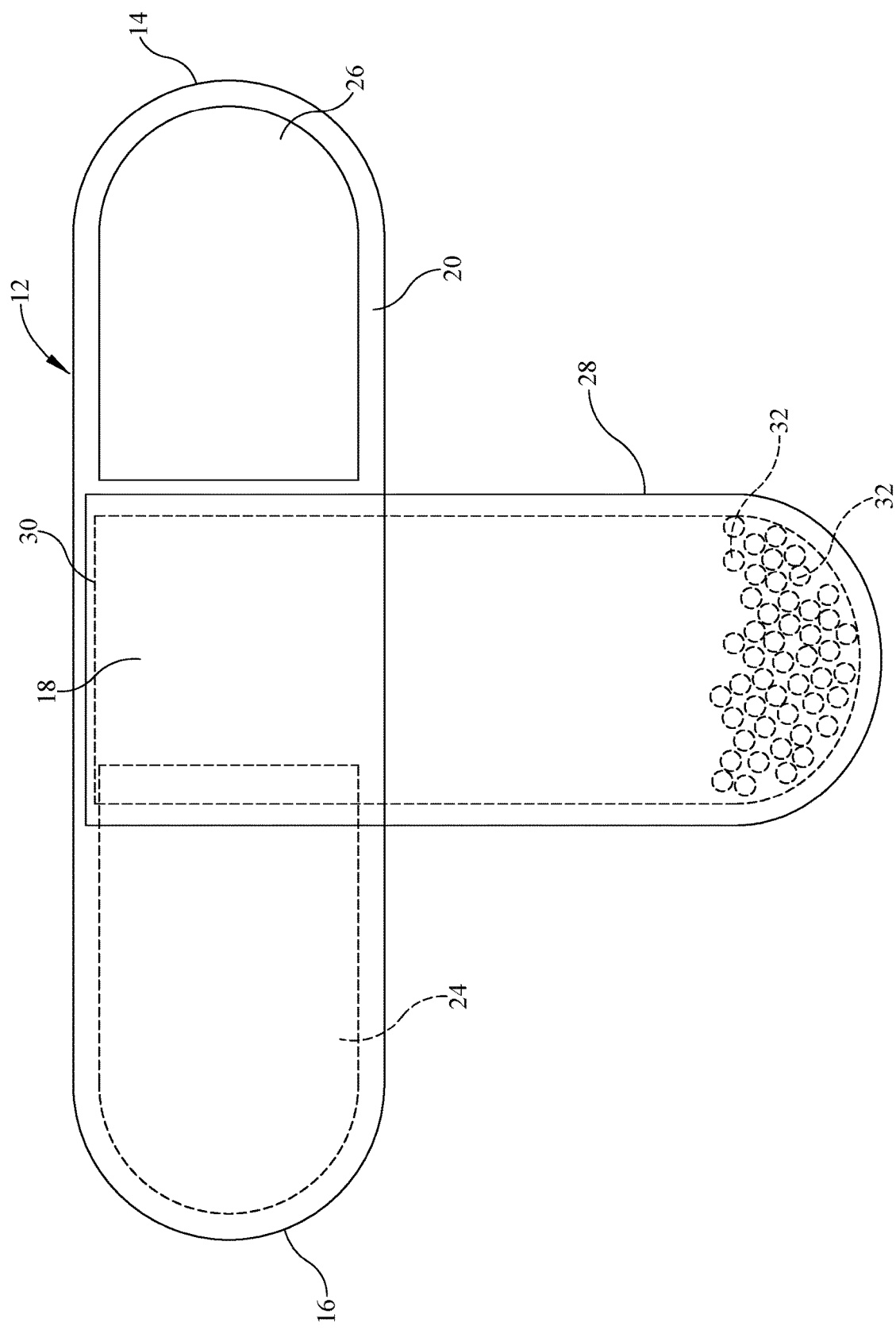
FIG. 3 is a front view of the male exercise device.

Referring now to the drawings, it is seen that the male exercise device of the present invention, generally denoted by reference numeral 10, is comprised of a band 12 that has a rounded first end 14 and an opposing rounded second end 16 with a medial section 18 therebetween. The band 12 has an upper surface 20 and an opposing lower surface 22. The band 12 is made from a stretch loop material that is a stretchy fabric made from a nylon elastomer (a combination of nylon and rubber, natural or synthetic) so that the band 12 stretches and retracts during usage. Additionally, the band 12 has a section of cooperating hook material 24 located on the upper surface 20 of the band 12 proximate the first end 14 and a corresponding section of loop material 26 located on the lower surface 22 of the band 12 proximate the second end 16. In addition to the rounded first end 14 and rounded second end 16, the band 12 has otherwise soft surfaces and rounded edges in order to be comfortable when worn against the skin of a user. A product produced under the trademarked name DuraGrip® by Velcro USA Inc., of Manchester N.H. is an example of commercially available stretch loop material.

A pocket 28 depends downwardly from the medial section 18 of the band 12. The pocket 28 is attached to the band 12 in any appropriate fashion such as via adhesion or the illustrated stitching 30. Located within the pocket 28 are a series of weight members 32 that give the device weight and thus resistance when worn. The weight members 32 can be any appropriate relatively dense members such as the illustrated zinc coated copper pellets that have a good weight to size ratio. Advantageously, the outer surfaces of the weight members 32 are smooth so as to not cause unnecessary poking or friction if pressed against a body part.

Figure 4:
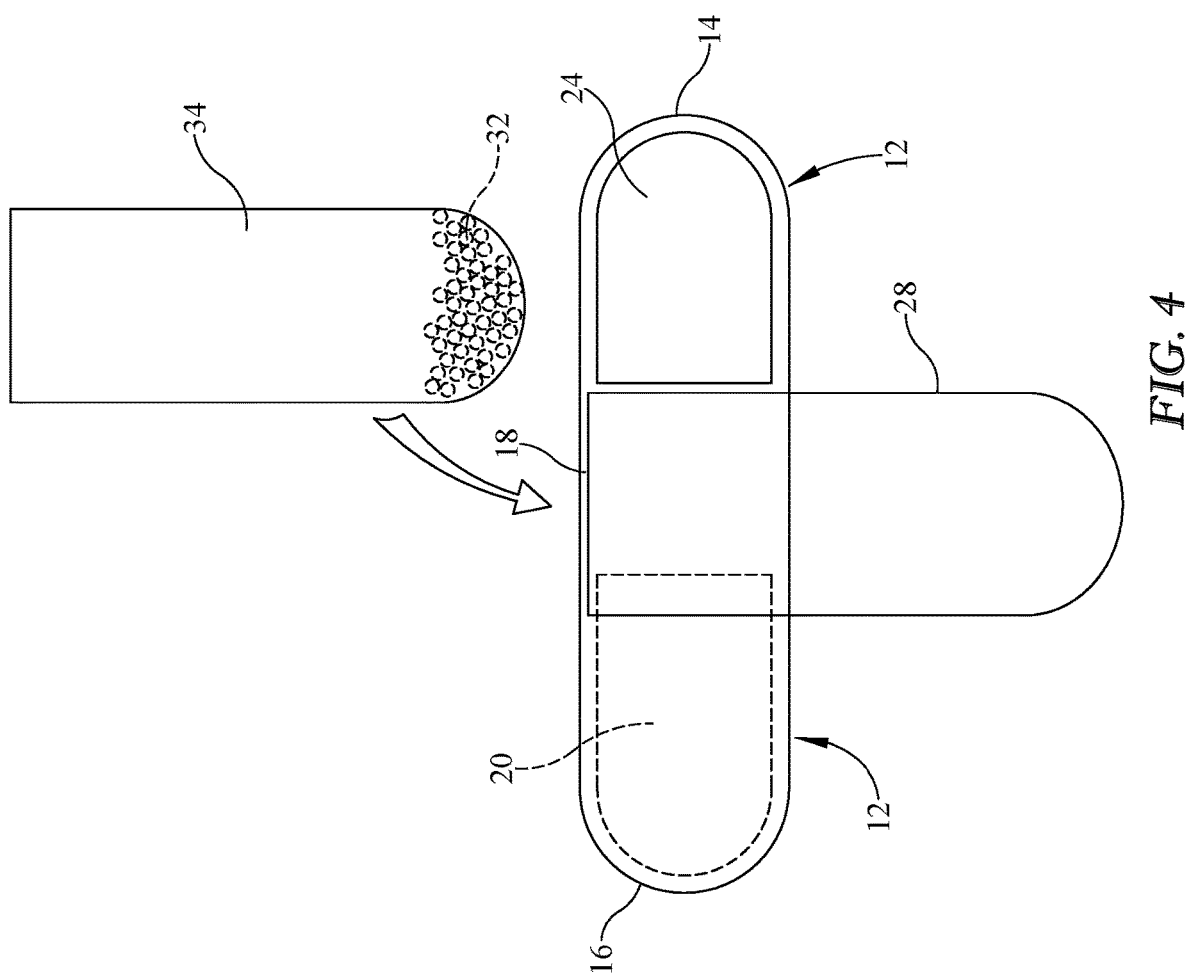
FIG. 4 is a front view of the male exercise device using a removable weight pouch.

The weight members 32 can be placed into the pocket 28 and the pocket 28 sealed so that the weight members 32 reside permanently within the pocket 28, or as illustrated in FIG. 4, the weight members 32 can be located within a satchel 34 that itself is sealed and the satchel 34 is placed into the pocket 28 and removed as needed. The use of a satchel 34 allows the user to change the weight of the male exercise device 10 by removing one satchel 34 from the pocket 28 and inserting a different satchel 34 having a different weight back into the pocket 28.

In order to use the make exercise device 10 of the present invention, the user selects a desired device (the user may have more than one male exercise device 10 each with a different weight) or can select a satchel 34 with the desired weight and place the satchel 34 into the pocket 28. The user then encircles the band 12 about his penis and secures the band 12 in this encircled position via the use of the cooperating hook section 24 and loop section 26 which are mated with one another in the usual way in order to hold the band 12 in the encircled position. The user performs any desired exercises. If the user's penis expands during exercising, the use of the stretch loop material for the band 12 allows the band 12 to stretch accordingly in an even and comfortable manner and thereafter retract with the retraction in size of the user's penis. The user can perform any desired exercises while wearing the male exercise device 10 or can simply maintain the device installed about his penis and allow the device to exercise the penis through the resistance afforded by gravity. When use of the male exercise device 10 is finished, the device is doffed by detaching the hook section 24 from the loop section 26 in the usual way and removing the device from the penis.

While the invention has been particularly shown and described with reference to an embodiment thereof, it will be appreciated by those skilled in the art that various changes in form and detail may be made without departing from the spirit and scope of the invention.

I claim:

1. A male exercise device adapted to encircle a penis in order to provide a weight for use during exercise of the penis, the male exercise device comprising:
   a planar band having a first end and a second end with a medial section disposed between the first end and the second end, the planar band also having an upper surface and a corresponding lower surface, the planar band also having an outer edge extending about an outer periphery of the planar band, the planar band being formed from a stretch loop material, the outer edge band having a straight upper edge extending between the first end and the second end and a straight coextensive lower edge extending between the first end and the second end;
   a section of cooperating hook material located on the upper surface of the planar band proximate to the first end;
   a section of cooperating loop material located on the lower surface of the planar band proximate to the second end;
   a pocket attached to the planar band and depending downwardly from the lower edge of the outer edge at the medial section of the planar band; and
   a series of weight members disposed within the pocket.

2. The male exercise device as in claim 1 wherein the outer edge is rounded at each of the first end and the second end of the planar band.

3. The male exercise device as in claim 1 wherein the series of weight members are metal pellets.

4. The male exercise device as in claim 3 wherein the metal pellets are made from zinc coated copper.

5. The male exercise device as in claim 1 wherein the series of weight members are located within a satchel, the satchel being removably received within the pocket.

* * * * *